United States Patent [19]
Skinner

[11] Patent Number: 5,606,140
[45] Date of Patent: Feb. 25, 1997

[54] QUALITY CONTROL APPARATUS AND METHOD

[76] Inventor: James A. Skinner, 14465 Old State Rd., Middlefield, Ohio 44062

[21] Appl. No.: 456,677

[22] Filed: Jun. 1, 1995

[51] Int. Cl.$^6$ ............................................. G01N 1/14
[52] U.S. Cl. ................ 73/864.81; 264/40.1; 264/142; 264/328.1; 425/557; 425/574; 425/585; 425/308
[58] Field of Search ..................... 73/863.84, 863.86, 73/864.34, 864.35, 863.11, 864.81; 264/40.1, 141, 142, 143, 328.1, 349; 425/135, 202, 207, 557, 574, 585, 586, 587, 308

[56] References Cited

U.S. PATENT DOCUMENTS

| | | |
|---|---|---|
| 3,278,988 | 10/1966 | Hannis . |
| 4,090,836 | 5/1978 | Von Der Ohe et al. ................. 425/574 |
| 4,098,649 | 7/1978 | Redker ................................. 264/349 |
| 4,262,533 | 4/1981 | Jaeger . |
| 4,756,855 | 7/1988 | Mathis et al. ......................... 264/40.7 |
| 4,890,996 | 1/1990 | Shimizu ................................ 425/311 |
| 4,908,168 | 3/1990 | Miller, Jr. et al. .................... 264/328.6 |
| 4,973,239 | 11/1990 | Herrmann et al. .................... 264/328.1 |
| 5,248,460 | 9/1993 | Tsutsumi ............................. 264/328.1 |
| 5,383,776 | 1/1995 | Trail et al. ........................... 425/135 |

FOREIGN PATENT DOCUMENTS 2246672   7/1974   Germany .

*Primary Examiner*—Jill L. Heitbrink
*Attorney, Agent, or Firm*—Watts, Hoffmann, Fisher & Heinke Co., L.P.A.

[57] ABSTRACT

An apparatus for the manufacture of plastic pellets including an extruder, a chiller positioned to receive and solidify extruded strands from the extruder and, a pelletizer for converting such strands to pellets. The apparatus includes a quality testing device having a valve connected to the extruder, an injector having a sample receiving position operably connected to the valve, and a sample mold for forming solidified test samples of the material for analysis. The injector also has an ejection position operably connected to a mold inlet for injecting such samples into the mold.

13 Claims, 2 Drawing Sheets

QUALITY CONTROL APPARATUS AND METHOD

FIELD OF THE INVENTION

This invention relates to plastic extrusion and more particularly to an extrusion system and process including a novel and improved quality control system.

BACKGROUND

In the manufacture of pelletized plastic for subsequent use in such applications as injection molding, strands of heat softened plastic are forced out of an extruder. Conventionally the strands then pass through a water bath to chill and solidify the extruded plastic. Chilled strands are then fed through a chopper which cuts the strands into small pellets for storage, shipment and subsequent use.

In known manufacturing processes the formed pellets are typically allowed to dry for about ½ hour and once dried samples are periodically taken for quality control testing. If it is determined that the material being extruded fails to meet quality specifications, such as, for example, lacking appropriate pigmentation to produce the desired finished color, literally hundreds of pounds of scrap may well have been produced before existing and standard quality control procedures identify the problem. Accordingly, there exists a need for an improved quality control apparatus and process in the formation of plastic pellets and other plastic products.

SUMMARY OF THE INVENTION

With the system of the present invention, a plastic control flow valve has an inlet coupled to an extruder by a heated conduit. A rotatably mounted injector is positioned in predetermined spaced relationship with the valve. The injector is selectively couplable to an outlet of the valve. When the injector and valve are so coupled, a valve member is unseated to establish flow from the extruder, through the valve and into the injector. The flow is of heated thermoplastic material and the flow is caused by pressure from the extruder.

Once a head of the injector has been filled with hot plastic, the head is retracted and the injector then rotates to align the head with a sampling mold. The head is then advanced to couple it to an inlet to a mold sprue. An injector plunger then forces plastic from the injector, through the sprue into a mold cavity. Once a sample so injected into the mold cavity has solidified, the sample mold is opened and the sample is analyzed for quality control.

Since the material drawn off as a quality control sample is taken directly from the extruder, material extruded into strands concurrently with the sample being taken may well have only reached the chopper by the time the test sample is solidified. Accordingly, any deficiency of the material being made into pellets is quickly determined and can be corrected promptly, thus avoiding the prior problem of manufacturing literally hundreds of pounds of defective product before a deficiency of that product was identified.

Accordingly, the objects of the invention are to provide a novel and improved plastic extrusion system with enhanced quality control and a method of controlling the quality of the product being formed.

DETAILED DESCRIPTION

Figure 1:
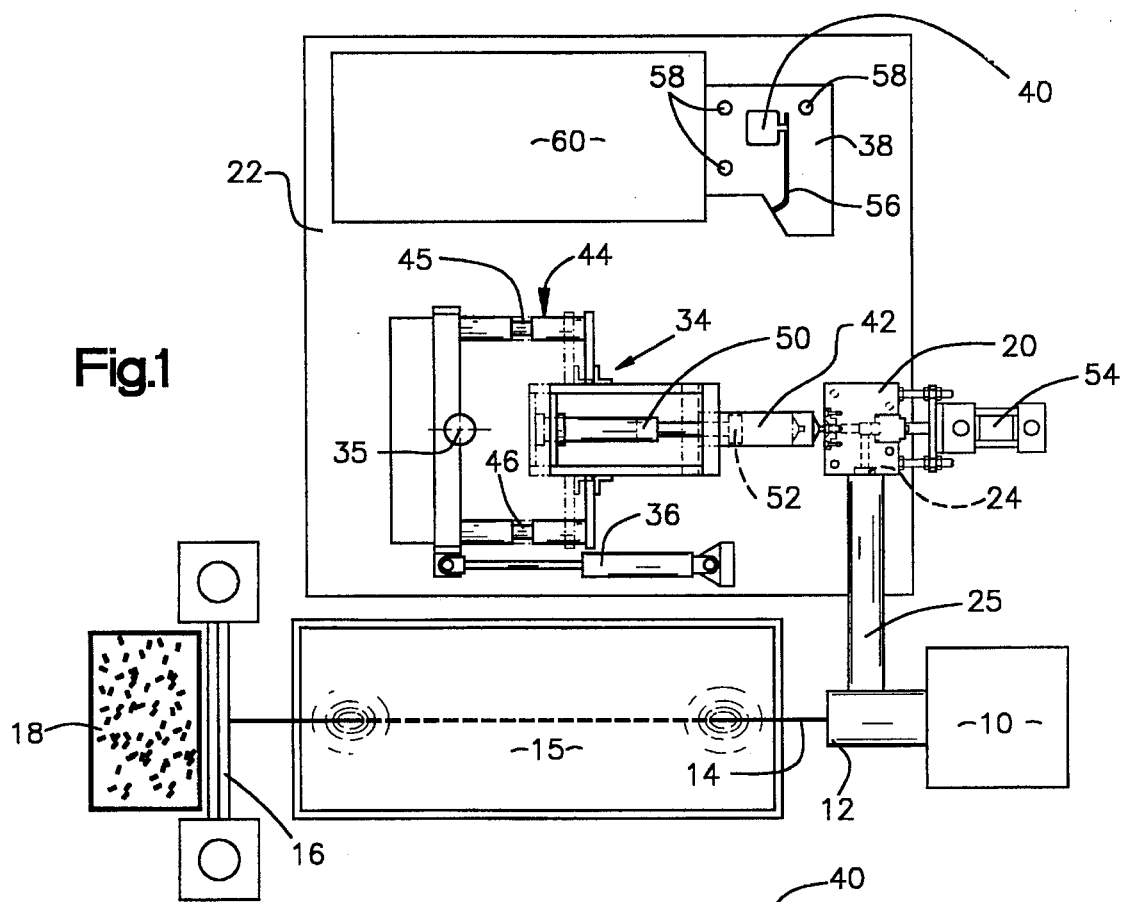
FIG. 1 is a somewhat diagrammatic top plan view of the quality control system of this invention with the injector positioned to receive material to be tested.
Figure 2:
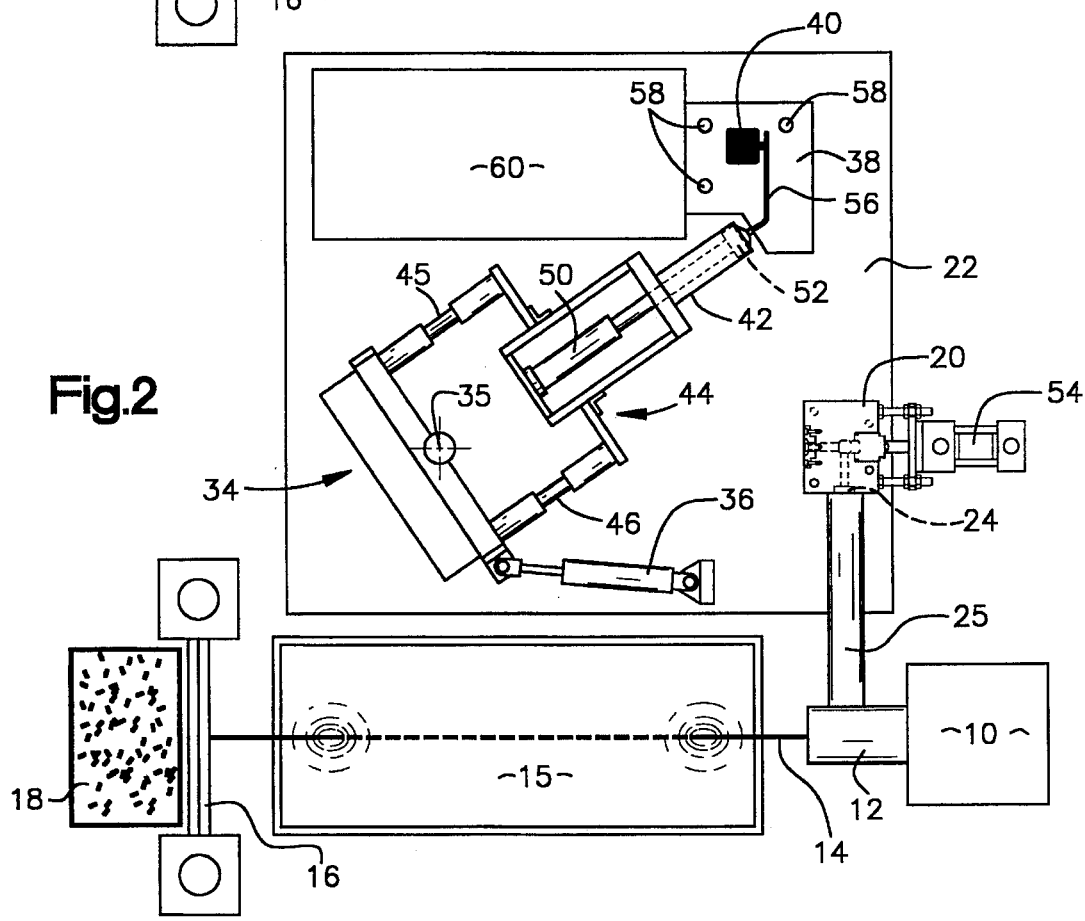
FIG. 2 is a view corresponding to FIG. 1 with the injector moved to its mold injection position; and, FIG. 3 is a partially sectioned view, and on an enlarged scale, of the valve used in the system of the present invention.

Referring now to the drawings and FIGS. 1 and 2 in particular, a heat softened, thermoplastic material supply mechanism in the form of an extruder 10 is provided. The extruder 10 is equipped with a die 12 for producing strands of plastic 14. The extruded strands 14 pass through a bath 15. On exiting the bath, the strands 14 enter a chopper 16 which deposits the plastic in pellet form into a pellet receiving receptacle 18. The extruder, bath, chopper and receptacle are all well known and conventional and hence shown generally schematically.

Figure 3:
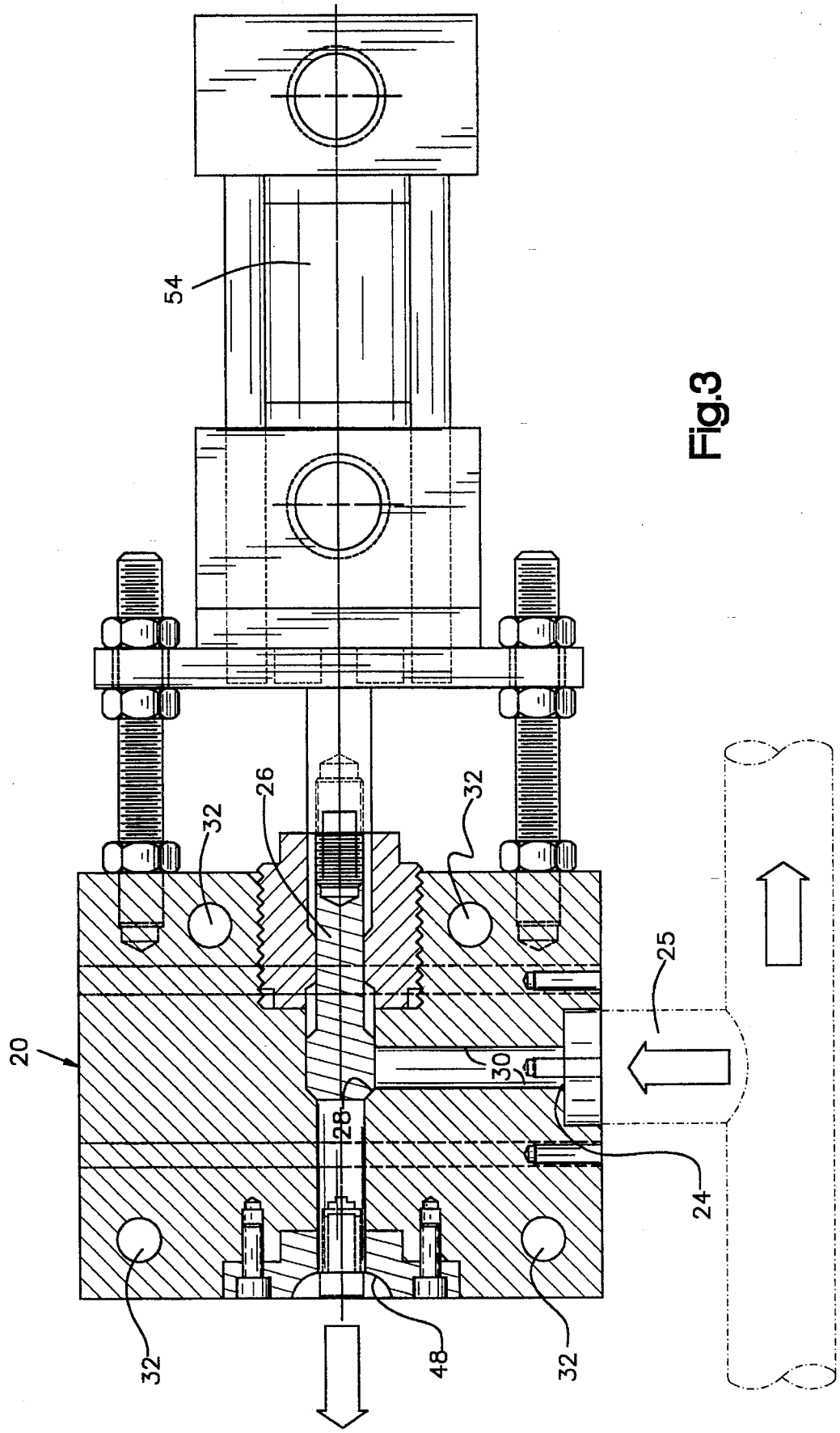

A sample vane 20 is provided. The sample vane 20 as shown is mounted on a frame 22. The vane 20 has an inlet 24 coupled to the extruder 10 by a heated conduit 25. The vane 20 includes a vane member 26 which normally engages a vane seat 28, FIG. 3. When the system is in use, heat softened plastic from the extruder fills the conduit 25 and an internal passage 30 of the vane 20. Thus, heat softened plastic under pressure is normally against the vane member 26 and maintained in its heat softened condition by the heating of the conduit 25 and heaters 32 in the vane 20.

An injector assembly 34 is provided. The assembly 34 is rotatably mounted on the frame 22 by a pivot 35. An actuator in the form of a fluid cylinder 36 is interposed between the frame 22 and the injector assembly 34 to rotatably move the assembly between its vane engaging position of FIG. 1 and its mold engaging position of FIG. 2.

A sample mold 38 is also carried by the frame 22. The sample mold delineates a sample cavity 40.

The injector assembly 34 includes an injector 42. The injector 42 forms a part of an injector subassembly 44. The subassembly has a retracted position shown in phantom in FIG. 1. When the injector subassembly 44 is in retracted position, the injector assembly can be pivoted between its vane aligned position of FIG. 1 and its mold aligned position of FIG. 2 and return.

When the injector assembly 34 has been moved to its vane aligned position of FIG. 1, subassembly actuators 45, 56 are extended to move the subassembly 44 including the injector 42 to the right as viewed in FIG. 1. This movement brings the injector into engagement with a vane outlet 48. At this juncture a ram or plunger actuator 50 which forms a part of the injector subassembly 44 is collapsed to move a plunger 52, FIG. 1, to a retracted position.

A valve actuator 54 is then energized to retract the valve member 26 and communicate the passage 30 with the valve outlet 48. Heat softened plastic then flows from the extruder via the conduit 25 and the passage 30 into the injector to fill a cavity forward, or to the right as viewed in FIG. 1, of the plunger 52. Once the injector has been supplied with a sufficient sample of the material, the valve member 26 is moved back to its closed position against the valve seat 28 and the actuators 45, 46 move the subassembly 44 to the left as viewed in FIG. 1 to the position shown in phantom lines.

The pivot actuator 36 then swings the injector assembly 34 to its mold aligned position of FIG. 2. The subassembly actuators 45, 46 are then extended to advance the injector into engagement with the mold 38 and communicate the injector cavity with a mold sprue 56. The plunger actuator 50 is then actuated to drive the plunger 52 from its position shown in FIG. 1 to the position shown in FIG. 2, thereby filling the mold cavity 40 as indicated by the darkened area of FIG. 2. If desired, cooling passages are provided in the mold 38 to accelerate the solidification of a sample to be tested. Once the sample is solidified, the mold is opened and the sample can be tested by any suitable and known test procedures.

A control panel 60 is provided. The control panel 60 controls the heating of the valve 20 and the conduit 25, the cooling of the mold 38 and the positioning of the injector assembly and its components.

OPERATION

In operation the vane actuator 54 will be energized to unseat the valve member 26 and allow fluid flow until the passage 30 is filled with material. Fluid flow is continued long enough to purge any residue from previously sampled plastic formulations. If there has been a change in material, the injector may also be filled and cycled until material from prior tests has been expelled. Once the extruder 10 is operating with a given supply of plastic and old material has been purged from the test system, the entire machine is ready for production.

Periodically as pellets are being formed, the extrusion assembly 34 is brought to its valve aligned position of FIG. 1. The plunger actuator 50 is operated to retract the plunger 52 and the subassembly actuators 45, 46 are actuated to move the injector into its valve engagement position of FIG. 1.

Once the injector is in engagement with the valve outlet 48, the valve actuator 54 is energized to retract the valve member 26 so that plastic to be sampled flows into and fills the injector 42. The valve member 26 is then moved to its closed position, the subassembly actuators 45, 46 retract the subassembly 44 to its phantom position of FIG. 1 and the position actuator moves the injection assembly 34 to its mold aligned position of FIG. 2. The subassembly actuators then extend the subassembly 44 into the mold engaging position of FIG. 4. The plunger actuator 50 then drives the plunger 52 outwardly, expelling the sample material from the injector through the sprue 56 and then into the mold cavity 40 to form a sample to be tested.

Although the invention has been described in its preferred form with a certain degree of particularity, it is understood that the present disclosure of the preferred form has been made only by way of example and that numerous changes in the details of construction, operation and the combination and arrangement of parts may be resorted to without departing from the spirit and the scope of the invention as hereinafter claimed.

What is claimed is:

1. A process of making periodically tested plastic products comprising:
    a) ejecting heat softened plastic material from a plastic processing machine;
    b) as the material is being ejected allowing the pressure of ejection to divert relatively small samples of the heat softened plastic to an injector via a sampling valve;
    c) moving the injector from a position communicating with the sampling valve to a mold communication position;
    d) injecting sample material from the injector into a sample mold; and,
    e) forming a test piece of the material by cooling the material in the mold.

2. The process of claim 1 further including the step of analyzing the test piece.

3. The process of claim 1 further including the steps of periodically repeating steps (b), (c) and (d) to sequentially and periodically form test pieces.

4. A system for quality analysis of thermally softened plastic material comprising:
    a) a valve means for operative connection to plastic supply mechanism, the valve means also being for unidirectional flow of material from the supply to and through the valve means;
    b) a sample mold for receiving quantities of material to be sampled;
    c) an injector having a fill position operatively connected to an output of the valve means for sequentially receiving quantities of material to be sampled and an injection position operatively connected to the mold for sequentially injecting such received materials to be sampled into the mold;
    d) a first prime mover for moving the injector between its fill and its injection positions; and,
    e) a second prime mover for actuating the injector to inject material into the mold.

5. The system of claim 4 wherein the vane is heated to maintain extruded material in a heat softened state.

6. The system of claim 4 wherein further material supplied from the extruder under pressure is utilized to force material from the valve into the injector when the valve and the injector are operatively connected.

7. The system of claim 4 further including means to chill the mold.

8. Apparatus for the manufacture of plastic pellets comprising:
    a) an extruder for ejecting strands of plastic material;
    b) a chiller positioned to receive and solidify extruded strands from the extruder;
    a pelletizer downstream from the chiller for converting such strands to pellets; and,
    d) a quality testing device for enabling frequent analysis of physical properties of material being extruded comprising:
        i) a valve having an inlet connected to the extruder for receiving samples of material ejected from the extruder;
        ii) an injector having a sample receiving position operably connecting the injector to an outlet of the valve;
        iii) a sample mold for forming solidified test pieces of samples of the material for physical property analysis;
        iv) the injector having an injection position operably connected to a mold inlet for injecting such samples into the mold;
        v) a first prime mover for shifting the injector back and forth between its sample receiving and its injection positions; and,
        vii) a second prime mover for injecting material from the injector into the mold.

9. The apparatus of claim 8 wherein the valve is heated to maintain extruded material in a heat softened state.

10. The apparatus of claim 8 wherein further material supplied from the extruder under pressure is utilized to force material from the valve into the injector when the valve and the ejector are operatively connected.

11. The apparatus of claim 8 further including means to chill the mold.

12. The apparatus of claim 8 wherein the first prime mover is a fluid cylinder.

13. A sampling system for use in quality control of a supply of thermoplastic material comprising:
   a) a frame structure;
   b) an injector mechanism movably mounted on the structure, the mechanism including an injector;
   c) a sampling valve mounted on the structure, the valve including an inlet for connection to a heat softened plastic supply machine and an outlet for periodic and selective connection to the injector;
   d) a sample mold connected to the structure and including an inlet for receiving material to be sampled from the injector; and,
   e) the injector including:
      i) a first prime mover for moving the injector between a valve coaction position and a mold coaction position;
      ii) a second prime mover for moving injector between retracted position and mold and valve engaging positions; and,
      iii) a third prime mover for readying the injector to receive material when the injector is in its valve engaging position and for injecting material into the mold when the injector is in its mold engaging position.

* * * * *